United States Patent
Ko

(10) Patent No.: US 11,311,739 B2
(45) Date of Patent: Apr. 26, 2022

(54) ELECTROMAGNETIC METHOD FOR IN-VIVO DISRUPTION OF VIRAL INSULTS

(71) Applicant: Harvey Wayne Ko, Ellicott City, MD (US)

(72) Inventor: Harvey Wayne Ko, Ellicott City, MD (US)

(*) Notice: Subject to any disclaimer, the term of this patent is extended or adjusted under 35 U.S.C. 154(b) by 0 days.

(21) Appl. No.: 17/443,878

(22) Filed: Jul. 28, 2021

(65) Prior Publication Data

US 2021/0370085 A1  Dec. 2, 2021

Related U.S. Application Data

(60) Provisional application No. 63/032,369, filed on May 29, 2020.

(51) Int. Cl.
| | | |
|---|---|---|
| *A61N 2/00* | (2006.01) | |
| *A61N 2/06* | (2006.01) | |
| *C12N 13/00* | (2006.01) | |

(52) U.S. Cl.
CPC ............ *A61N 2/004* (2013.01); *A61N 2/002* (2013.01); *A61N 2/06* (2013.01); *C12N 13/00* (2013.01)

(58) Field of Classification Search
CPC ............... A61K 49/227; A61K 9/0009; A61K 47/6923; A61K 47/6929; A61K 39/3955; A61N 2/02; A61N 2/002; A61N 2/00
See application file for complete search history.

(56) References Cited

U.S. PATENT DOCUMENTS

| | | | | |
|---|---|---|---|---|
| 2005/0090732 A1* | 4/2005 | Ivkov | ...................... | A61P 43/00 600/411 |
| 2010/0099942 A1* | 4/2010 | Portelli | .................... | A61N 2/02 600/13 |
| 2011/0182805 A1* | 7/2011 | DeSimone | .............. | A61P 29/00 424/1.11 |

(Continued)

OTHER PUBLICATIONS

Ko, H. W. (May 21, 1973). Magnetically Induced Birefringence in Nematic Lquid Crystals (Dissertation, Drexel University, 1973) [Abstract].

(Continued)

*Primary Examiner* — Christine H Matthews
*Assistant Examiner* — Joshua Daryl D Lannu
(74) *Attorney, Agent, or Firm* — Dunlap Bennett & Ludwig, PLLC; Anna L. Kinney

(57) ABSTRACT

A therapeutic method of reducing or eliminating viral infections in vivo includes subjecting a virally infected patient to one of a variety of strong magnetic fields. A static magnetic field has a magnetic field intensity of at least about 5 nanoTesla sufficient to be effective to disrupt viral metabolism. An alternating magnetic field has a magnetic field intensity of at least 0.1 nanoTesla sufficient to be effective to disrupt viral metabolism. A method of disrupting viral metabolism includes subjecting an infected patient or a mixture of live host cells and virus to the alternating magnetic field. A virus disruption apparatus includes a magnetic field generator of static or alternating magnetic fields. The magnetic field generator is selected from a Magnetic Resonance Imaging device, at least one permanent magnet, at least one superconducting magnet, at least one solenoid, and any combination thereof.

16 Claims, 4 Drawing Sheets

(56) References Cited

U.S. PATENT DOCUMENTS

| | | | | |
|---|---|---|---|---|
| 2012/0010454 A1* | 1/2012 | Lamb | ............... | A61N 2/12 600/10 |
| 2013/0090515 A1* | 4/2013 | Chang | ............... | A47C 31/003 600/9 |
| 2015/0105607 A1* | 4/2015 | Feng | ............... | A61N 2/008 600/13 |

OTHER PUBLICATIONS

OpenStaxCollege. (Aug. 22, 2012). Virus infections and hosts. Retrieved Jul. 26, 2021, from http://pressbooks-dev.oer.hawaii.edu/biology/chapter/virus-infections-and-hosts/.

Corum, J., & Zimmer, C. (Apr. 3, 2020). Bad news wrapped in protein: Inside the coronavirus genome. Retrieved Jul. 26, 2021, from https://www.nytimes.com/interactive/2020/04/03/science/coronavirus-genome-bad-news-wrapped-in-protein.html.

Melikyan, G. B. (2010). Driving a wedge between viral lipids blocks infection. Proceedings of the National Academy of Sciences, 107(40), 17069-17070. doi:10.1073/pnas.1012748107.

Rosenblatt, C., Yager, P., & Schoen, P. (1987). Orientation of lipid tubules by a magnetic field. Biophysical Journal, 52(2), 295-301. doi:10.1016/s0006-3495(87)83216-2.

Drakesmith, H., & Prentice, A. (2008). Viral infection and iron metabolism. Nature Reviews Microbiology, 6(7), 541-552. doi:10.1038/nrmicro1930 [Abstract].

Barbie, M. (2019). Possible magneto-mechanical and magneto-thermal mechanisms of ion channel activation in magnetogenetics. doi:10.7554/elife.45807.013.

Zablotskii, V., Polyakova, T., Lunov, O., & Dejneka, A. (2016). How a high-gradient magnetic field could affect cell life. Scientific Reports, 6(1):37407. doi:10.1038/srep37407.

Almstätter, I., et al. (2015). Characterization of magnetic viral complexes for targeted delivery in oncology. Theranostics, 5(7), 667-685. doi:10.7150/thno.10438.

Tang, J., Alsop, R., Schmalzl, K., Epand, R., & Rheinstädter, M. (2015). Strong static magnetic fields increase the gel signal in partially hydrated DPPC/DMPC membranes. Membranes, 5(4), 532-552. doi:10.3390/membranes5040532.

Ko, H. W., Gianni, J. A., & Herchenroeder, P. J. (1982). Oceanographic Elf Electromagnetic Investigations at APL. John Hopkins APL Technical Digest, 3(1), 59-66.

Meister, M. (2016). Physical limits to magnetogenetics. ELife, 5. doi:10.7554/elife.17210.

Powell, A. E., et al. (2020). A single immunization with spike-functionalized ferritin vaccines elicits neutralizing antibody responses against SARS-CoV-2 in mice. doi:10.1101/2020.08.28.272518.

Ehsani, S. (2020). COVID-19 and iron Dysregulation: Distant sequence similarity Between Hepcidin and the novel Coronavirus Spike glycoprotein. Biology Direct, 15(1):19. doi:10.1186/s13062-020-00275-2.

Liu, W., Zhang, S., Nekhai, S., & Liu, S. (2020). Depriving iron supply to the virus represents a promising adjuvant therapeutic against viral survival Current Clinical Microbiology Reports, 7(2), 13-19. doi:10.1007/s40588-020-00140-w.

Christiansen, M. G., Hornslien, W., & Schuerle, S. (2020). A possible inductive mechanism for magnetogenetics. doi:10.1101/2020.07.16.207126.

Aminul Islam, M., & Ziaul Ahsan, M. (2020). Possible therapeutic approach against COVID-19 by application of magnetic field. American Journal of Nanosciences, 6(3), 18-23. doi:10.11648/j.ajn.20200603.11.

Huang, Y., Yang, C., Xu, X., Xu, W., & Liu, S. (2020). Structural and functional properties of SARS-CoV-2 Spike protein: Potential Antivirus drug development for COVID-19. Acta Pharmacologica Sinica, 41(9), 1141-1149. doi:10.1038/541401-020-0485-4.

Xue, L., Deng, D., & Sun, J. (2019). Magnetoferritin: Process, prospects, and their biomedical applications. International Journal of Molecular Sciences, 20(10), 2426. doi:10.3390/ijms20102426.

Goldsmith, C. S., & Miller, S. E. (2009). Modern uses of electron microscopy for detection of viruses. Clinical Microbiology Reviews, 22(4), 552-563. doi:10.1128/cmr.00027-09.

Christiansen, M. G., & Anikeeva, P. (2021). Magnetic fields for modulating the nervous system. Physics Today, 74(2), 28-34 doi:10.1063/pt.3.4677.

* cited by examiner

ELECTROMAGNETIC METHOD FOR IN-VIVO DISRUPTION OF VIRAL INSULTS

CROSS-REFERENCE TO RELATED APPLICATION

This application claims the benefit of priority of U.S. provisional application No. 63/032,369, filed May 29, 2020, the contents of which are herein incorporated by reference.

BACKGROUND OF THE INVENTION

The present invention relates to in-vivo disruption of viruses and, more particularly, to an electromagnetic method for disrupting viral insults in vivo.

Viruses such as Severe Acute Respiratory Syndrome (SARS), Human Immunodeficiency Virus (HIV), and Coronavirus Disease 2019 (COVID19) that invade the body often cannot be totally killed or have their metabolic processes totally disrupted or disabled by microbiology (Mi) such as antibodies and/or deoxyribonucleic acid (DNA)/ribonucleic acid (RNA) manipulations or by insertion of pharmacological drugs (Pcl). The development of new microbiology pharmacological drug (hereinafter denoted as MiPcl) compounds to deter new viruses or slightly different re-emergent strains of older viruses takes too long, if they are ever developed at all. The consequence is morbid.

All biological substances have a magnetic susceptibility that dictates how well the substances (a cell or cell groups) respond to the application of magnetic fields alternating in time (aka AC), or static in time (aka DC). Iron biological compounds like ferritin and ferroportin are especially sensitive to magnetic fields and can greatly amplify magnetic field effects. Ferritin and ferroportin are key to transportation of ions in the body and life support metabolism. Many viral spike proteins metabolize iron substances embedded in host cells as their primary method for host attachment and infection.

An electromagnetic resonant cavity is formed between the surface of the Earth and the Earth's ionosphere. Magnetic fields from electromagnetic waves inside this cavity occur at several ultralow or extremely low frequencies, such as 7.8±0.5 Hertz (Hz), or about 8 Hz and higher harmonics up to about 32 Hz. Schumann Resonances are ambient electromagnetic waves that exist in this cavity, with resonant amplitudes larger than adjacent frequencies (i.e., below 8 Hz and above 32 Hz). The Schumann resonances are the principal cause of Earth's ambient or "normal" alternating magnetic field (ACHe) and have amplitudes on the order of a picoTesla=$1E^{-12}$ Tesla (T). Of course, almost everything, including viral particles, is perpetually immersed in these ACHe magnetic fields. It is believed that the biorhythm of the human brain at 8 Hz is one evolutionary outcome of this exposure. One Tesla (T)=10,000 Gauss=$1 \times E^9$ gamma, is a measure of magnetic field intensity.

Earth's ambient or "normal" static (i.e., zero frequency) magnetic field (aka DCHe) that surrounds the Earth is approximately 0.4 G=$4 \times 10^{-5}$ Tesla (T)=40 microTesla. Caused by the rotation of Earth's molten core, this DCHe is known for its use in compass navigation.

Manmade magnetic field intensities range widely. For example, manmade radiofrequency (RF) fields (such as radio, TV, communications) are approximately 0.1 microTesla. Manmade power distribution lines are about $20 \times 10^{-6}$ Tesla or about 20 microTesla. Magnetic resonance imaging (MRI) operates at approximately 2 to 5 Tesla, direct current (DC). Permanent magnets for heavy lifting and attachment procedures, and within cyclotron resonance instruments are about 1 to 3 Tesla, DC. High alternating electrical current (AC) with water cooled wire coils are approximately ½ Tesla @ 10 Hz. Strong Magnetic Field (SMF) of several billion times the natural magnetic fields of earth are readily available.

The effects of very high magnetic fields on biological systems at the cellular level are not well understood (e.g., Magnetogenetics). There is a void of knowledge of the amplitude, spatial gradient, and rapid on-off switching changes on cellular function and morphology. Certain Strong Magnetic Field (SMF) systems (e.g., cyclotron resonance, MRI) have been used for mass spectroscopy and structural imaging but not for in-vivo analysis of whole viruses or in-vivo patient therapy. There are no SMF systems intended as countermeasures to viral metabolism, especially in-vivo. There are no existing SMF systems (on the order of several Tesla, i.e., over 100,000 times the natural magnetic fields of the Earth) utilized to totally disrupt or disable viral metabolism, especially in-vivo.

As can be seen, there is a need for new, non-MiPcl therapies to help defeat viral infection and to augment MiPcl therapies, enabling them to be more penetrating and/or faster in countering a viral infection.

SUMMARY OF THE INVENTION

Many of the SMF apparatuses cited herein have already been deployed safely (e.g., MRI; cyclotron resonance) but only for anatomical structural imaging or analytical spectrographic functions. Therefore, the present invention and accompanying methodologies may provide effective in-vivo anti-viral therapy with viral disruption to save lives NOW while MiPcL substances are developed and tested over a period of months to years. New in-vivo therapy practices, devices and systems may also result due to the invention.

In one aspect of the present invention, a therapeutic method of reducing or eliminating viral infections in vivo is provided, comprising subjecting a virally infected patient to a static magnetic field with a magnetic field intensity of at least about 5 nanoTesla sufficient to be effective to disrupt viral metabolism.

In another aspect of the present invention, a method of disrupting viral metabolism is provided, comprising subjecting an infected patient (for in-vivo therapy) or a live host cell and viral mixture (for therapy diagnostics and design) to an AC magnetic field with a magnetic field intensity of at least 0.1 nanoTesla sufficient to be effective to disrupt viral metabolism.

In another aspect of the present invention, a virus disruption apparatus is provided, comprising a magnetic field generator selected from the group consisting of: a Magnetic Resonance Imaging device, at least one permanent magnet, at least one superconducting magnet, a cyclotron, at least one solenoid, and any combination thereof.

These and other features, aspects and advantages of the present invention will become better understood with reference to the following drawings, description, and claims.

DETAILED DESCRIPTION OF THE INVENTION

Figure 1:
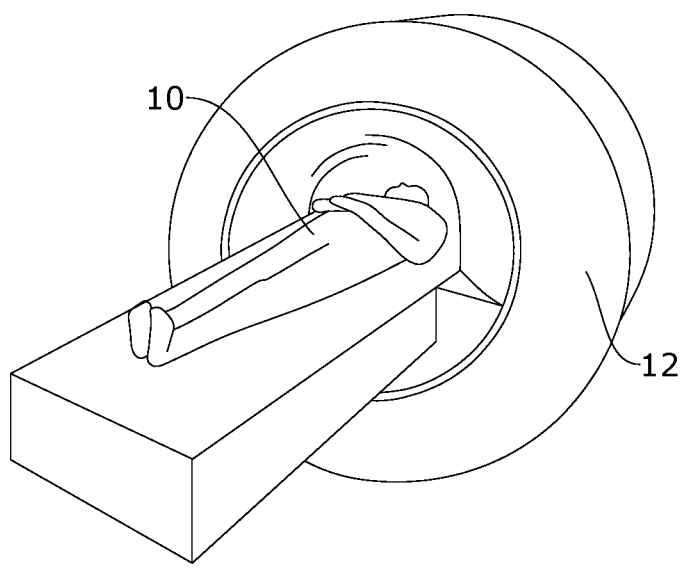
FIG. 1 is a perspective view of a method of viral disruption according to an embodiment of the present invention, showing a subject lying within a magnetic resonance imaging system.

The following detailed description is of the best currently contemplated modes of carrying out exemplary embodiments of the invention. The description is not to be taken in a limiting sense but is made merely for the purpose of illustrating the general principles of the invention, since the scope of the invention is best defined by the appended claims.

Broadly, one embodiment of the present invention is a quick therapeutic method of disrupting viral infections by applying SMF in-vivo to virally infected subjects, using either zero frequency (in other words, a magnetic field with a static magnitude which may be induced by direct current [DC]) or alternating frequency (which may be induced by an alternating current [AC]) magnetic fields that are anywhere from a multiple of 100,000 times (for static ambient Earth's fields) to 10 billion times (for alternating ambient Earth's fields) to which viral particles are otherwise exposed.

All substances, especially lipid proteins, possess a magnetic susceptibility (regardless of whether iron-based compounds are present) that gauges the substance's ability to react to magnetic fields.

Without being bound by theory, this magnetic susceptibility enables strong magnetic fields (SMF) to change orientation, cause alignment called field induced anisotropy, perhaps cause increased volumetric magnetic polarization, create forces on moving components (V×B), induce magnetic moment attraction/repulsion with other magnetically affected substances in proximity, and cause structural changes that disrupt cell function. This disruption may be in/amongst virions (e.g., spike proteins) themselves or with host cell components such as the iron-laden ferritin. Spatial and time gradient (i.e., AC or on/off switching) may increase particle acceleration and forces, enable particle/protein rotation, and induce homopolar generation to enhance disruption. See Zablotskii, V., et al., "How a High-Gradient Magnetic Field Could Affect Cell Life", Scientific Reports, 18 Nov. 2016; openstax, Chapter 21.2 Virus Infection and Hosts, "Viral evolution, morphology, and classification", Rice University, accessed online April 2020; Corum, J., et al., "Bad news wrapped in protein: inside the coronavirus genome", www.nytimes.com, 3 Apr. 2020; Ko, H. W, et al., "ELF Oceanographic Investigations at APL", APL Tec Dig.; Meister, M, "Physical limits to magnetogenetics", e Life, 2016; Powell, A. E., et al., "A Single Immunization with Spike-Functionalized Ferritin Vaccines Elicits Neutralizing Antibody Responses against SARS-Co-2 in Mice", ACS Cent. Sci., 7, 183-199, 2021; Ehsani, S, "COVID19 and iron dysregulation: distant sequence similarity between hepcidin and the novel coronavirus spike glycoprotein", Biology Direct, 15:19, 2020; Liu, W., et al "Depriving Iron Supply to the Virus Represents a Promising Adjuvant Therapeutic Against Viral Survival", Curr Clinical Microbiol. Rpts, 20 Apr. 2020; Christiansen, M., et al, "A Possible Inductive Mechanism for Magnetogenetics", doi.org, 17 Jul. 2020; Islam, A. et al., "Possible Therapeutic Approach Against Covid-19 by Application of Magnetic Field", Amer. of Neurosciences, 6, 18-23, 2020; Huang, Y. et al., "Structural and functional properties of SARS-CoV-2 spike protein:" Acta Pharmacolo. Sinica., 41, 1141-1149, 2020; Xue, L., et al "Magnetoferritin: Process, Prospects, and their Biomedical Applications", Int Journ. Molecular Sci, 16, May 2019 and Goldsmith, C., et al., "Modern Uses of Electron Microscopy for Detection of Viruses", Clinical Microbiol. Rev. 552-563, October 2009, the disclosures of which are incorporated herein in their entirety by reference, describe these features in detail and the latter offers suggestions for evaluating the benefit of these SMF countermeasures.

Without being bound by theory, Strong Magnetic fields (SMF) are believed to alter viral metabolic mechanisms, especially those that rely on iron-based substances. SMF are believed to disrupt the viral influence by either altering the structure of virions and/or virion captured host cells, especially when the host cells exude iron-based compounds such as ferritin and ferroportin, or by fragmenting the virus spike proteins and thereby disrupting the viruses' metabolism. This electromagnetic (EM) SMF modality is also believed effective to: re-orient the position and orientation of virions, disrupting the virus's metabolism; alter the number of viral spike proteins and host cell receptors needed to bind to host cells; change the orientation of clogging membrane cells to better admit the hydrodynamic flow and improve efficacy of MiPcL substances (thereby creating a viral "Achilles' heel"); cause captured/engulfed host cell substances (e.g., ferritin) to move/puncture viral membranes; and change ion channels to enhance different applied therapy chemistries. See Ko, H. W., "Magnetically Induced Birefringence in Nematic Liquid Crystals", PhD Dissertation, Drexel University, 1973; Melikyan, G. B.; "Driving a wedge between viral lipids blocks infection", PNAS, Vol. 107, No. 40, 5 Oct. 2010; Rosenblatt, C., et al.; "Orientation of lipid tubules by a magnetic field", Biophys. J. Biophysical Society, Vol 52, August 1987; Drakesmith, H., et al., "Viral infection and iron metabolism", Nature Reviews Microbiology, Vol 6, 2008; Barbic, M., "Possible magneto-mechanical and magneto thermal mechanisms of ion channel activation in magneto genetics", eLife, Vol 8, 2019; and Tang, J., et al, "Strong static magnetic fields increase the gel signal in partially hydrated DPPC/NMPC membranes", Membranes, 5, 2016, the disclosures of which are incorporated herein in their entirety by reference.

Alternating Magnetic (AM) Fields at least 1000× larger in size and frequency than naturally occurring fields are believed to result in reorientation of viruses due to: magnetic polarization of iron-based substances (e.g., ferritin); vibration changes; shape changes based on the reorientation and vibration; and explosive forces due to Lenz's law causing iron substances to pierce and break through spike protein membrane cells either destroying viral particles and/or spike proteins. These effects may enable infused chemistry (i.e., vaccines and drugs such as, but not limited to, antiviral pharmacological compositions administered before or during the exposure to a magnetic field) to work more effectively. Resonant motion of iron particulates may help induce and/or amplify vibrational changes and viral destroying properties with iron substances.

The present invention therapeutically exposes viruses to static magnetic fields (aka direct current [DC] magnetics) up to about 5 Tesla that are about $1\times10^5$ times or more the ambient static magnetic field of the Earth. The SMF may include Strong Alternating Magnetic (aka AC Magnetic) fields about $1\times10^{10}$ times the ambient alternating magnetic fields of the Earth. See Ko et al., "Oceanographic ELF Electromagnetic Investigations at APL", Johns Hopkins APL Technical Digest, Vol. 3, No. 1, 1982, pages 59-66. Preferably, frequencies in about the 7 to 32 Hz range may be tried first.

This invention employs Strong Magnetic Field (SMF) systems deemed medically safe (e.g., Magnetic Resonance Imaging [MRI], permanent magnets, superconducting magnet technology, cyclotron resonance, body solenoids [static SMF or alternating time SMF] and/or arm solenoids for blood borne viruses, and combinations thereof) to either disrupt the viral metabolic processes or to kill the virus outright, thereby countering morbid viral outcomes. The application of Strong Magnetic Fields (SMF) on the order of several Tesla (approximately $1\times10^5$ times the earth's ambient static magnetic field of about 50 microTesla) may be achieved by these means. Standard MiPcl assays known to those skilled in the art and electron microscopy may determine the efficacy of field strength and gradient modalities. The inventive systems generally use commercially available electrical engineering monitors such as ammeters, voltmeters, and oscilloscopes. For example, the method may employ a pre-existing MRI system and/or permanent magnets on a subject's body or to apply SMF to live cell and viral cultures within test tubes or petri dishes.

In some embodiments, a manufacturer may mount neodymium permanent magnets onto non-magnetic or non-metal substrates/slabs (e.g., plywood) to avoid eddy current and Lenz's law effects and may place the mounted magnets under and over the body organs of interest. This approach may be used to generate a static SMF or a time varying (aka AC or alternating) magnetic field.

In some embodiments, a large body treatment apparatus without MRI may be manufactured by fabricating large diameter long solenoidal coils, for example using commercially available 100 ampere house wirings. High DC current therefor may be provided, for example, by commercially available lead acid batteries (i.e., car batteries) or submarine batteries. Water or liquid nitrogen coolant may be circulated around the coils. Standard high current safety procedures known to those skilled in the art are advised (i.e., ammeters, resistive ballasts, non-arcing switches, etc.). Commercially available gaussmeters may be employed for SMF measurement.

In some embodiments, magnetic nanoparticles (MNP), presently used in oncology tracers, may be added to the host cell complex to further "poison" the hijacking virions and make them more vulnerable to magnetic disruption, i.e., amplify the effects of SMF treatment. See Almstatter, I., et al, "Characterization of magnetic viral complexes for targeted delivery in oncology", Theragnostic, 5 (7), 2015 and Tang, supra, the disclosure of which is incorporated herein by reference.

The inventive method may add tools and new virion analysis categories (e.g., protein EM susceptibility) to viral analyses. A method of analyzing effectiveness the present invention may include the following steps. Insert samples of virus with real host culture into the SMF (static=DC or alternating=AC). Add MiPcL substances to some samples to determine if the addition of SMF shows additional benefit beyond the MiPcl substances alone. Expose samples to SMF over a range of times from minutes to hours. Assess the viability of the virus metabolism with standard MiPcL methods known to those skilled in the art, such as petri dish stain analyses and/or electron microscopy methods. To determine effectiveness on a patient, have the patient lie down. Apply a strong magnetic field having characteristics selected due to results obtained with the cultured samples. Analyze the patient response and host cell changes with standard medical and MiPcL methods known to those skilled in the art. Repeat the same protocols with alternating magnetic field currents (i.e., AC Magnetics).

An example analysis of SMF effectiveness may comprise the following steps. Choose several different specimen types, e.g., including: a host with Virus A and no additives; a host with Virus A with a therapeutic additive; a host with Virus B and no additives; and a host with Virus B with the therapeutic additive. Obtain a visual baseline condition for each sample. Place the samples (e.g., 2 of each type) onto an SMF device above the magnet swing trail. Select a magnetic field frequency (e.g., 3, 8, 20 Hz) and 2 application time durations (e.g., about 10 to about 30 seconds) for the analysis. Turn the SMF device motor ON for approximately 30 seconds. Stop the SMF motor after the first selected duration and remove ½ of the specimen batch for analysis. Start and run the SMF motor for the second selected duration. Remove the remaining samples for analysis.

Referring to FIGS. 1 through 7, several apparatuses are shown suitable for therapeutic treatment to disrupt viruses. FIG. 1 shows a patient 10 within an MRI system 12 containing magnets that produce a SMF of about 3 to about 10 Tesla. Various magnetic field configurations, alternating and static, may be used.

Figure 2:
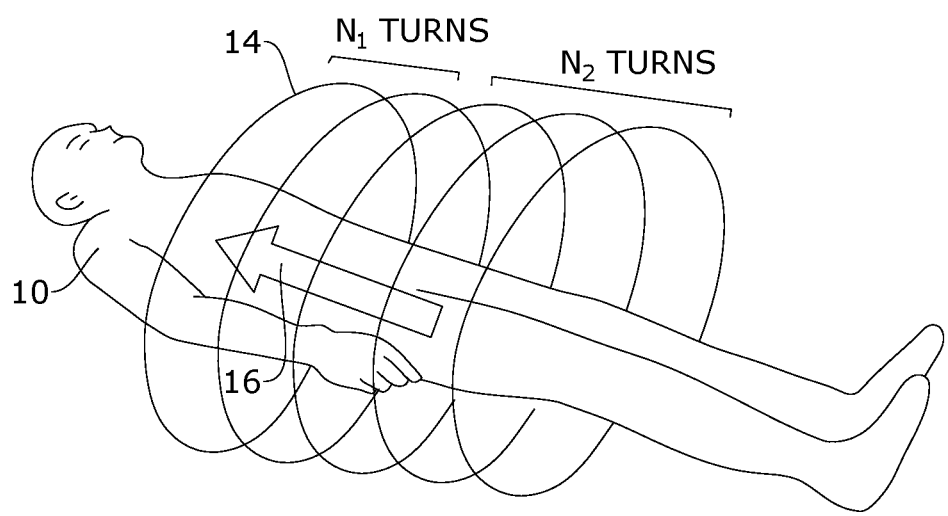
FIG. 2 is a schematic view of a method of viral disruption according to an embodiment of the present invention, showing a subject lying within a long multiturn solenoidal coil.

As shown in FIG. 2, a long, whole-body solenoid having a predetermined number of $N_1+N_2$ windings of current-carrying SMF coil 14 along its length coil surrounding the patient 10 may produce a magnetic field 16 of about ½ to about 3 Tesla, also using various alternating and static magnetic fields, with spatial gradient fields, suitable for treating affected body organs.

Figure 3:
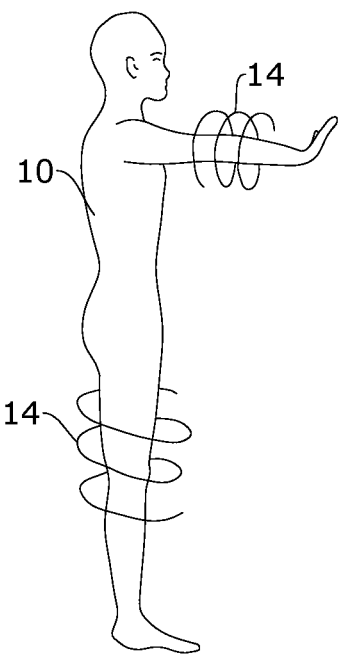
FIG. 3 is a schematic side view of a method of viral disruption around extremities according to an embodiment of the present invention, showing a subject's extremities encircled by a short solenoidal coil.

Blood borne viral insults may be treated with simpler SMF coils 14 or arrays of solenoids and/or permanent magnets that surround the patient's 10 arms and/or legs, as may be seen in FIG. 3. The magnetic fields applied in FIG. 3 may be either of AC or DC form.

Figure 4:
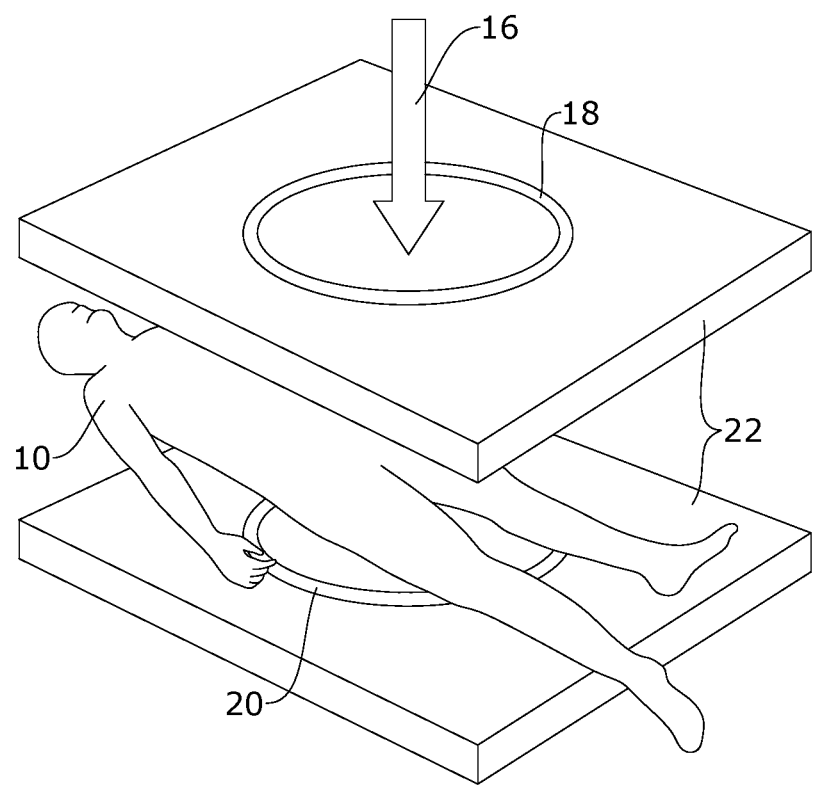
FIG. 4 is a schematic view of a method of viral disruption according to an embodiment of the present invention, showing a subject lying between a pair of lateral strong multiturn coil platforms.

A parallel pair of non-conducting, non-metallic coil platforms 22 or slabs comprising strong permanent magnet arrays as shown in FIG. 4, with an upper coil winding 18 and a lower coil winding 20, may produce a magnetic field 16 used to treat a patient 10 if high current electricity is not used. The magnetic fields applied in FIG. 4 may be either of AC or DC form.

Figure 5:
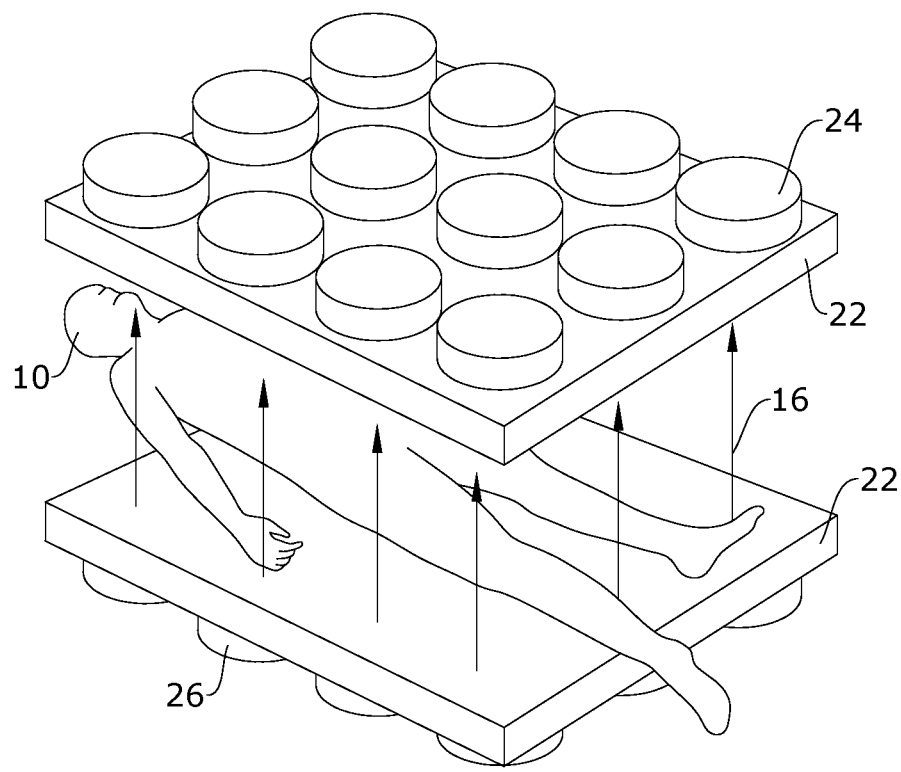
FIG. 5 is a schematic view of a method of viral disruption according to an embodiment of the present invention, showing a subject lying between a pair of strong permanent magnet platforms.

FIG. 5 shows two platforms 22 with numerous stationary strong permanent magnets 24, 26 comprising, e.g., Neodymium (i.e., static/DC magnetics), with the patient 10 placed therebetween subject to a magnetic field 16 of about 1 to about 2 Tesla. A mechanical insertion of high permeability shields enables on-off AC capability.

Figure 6:
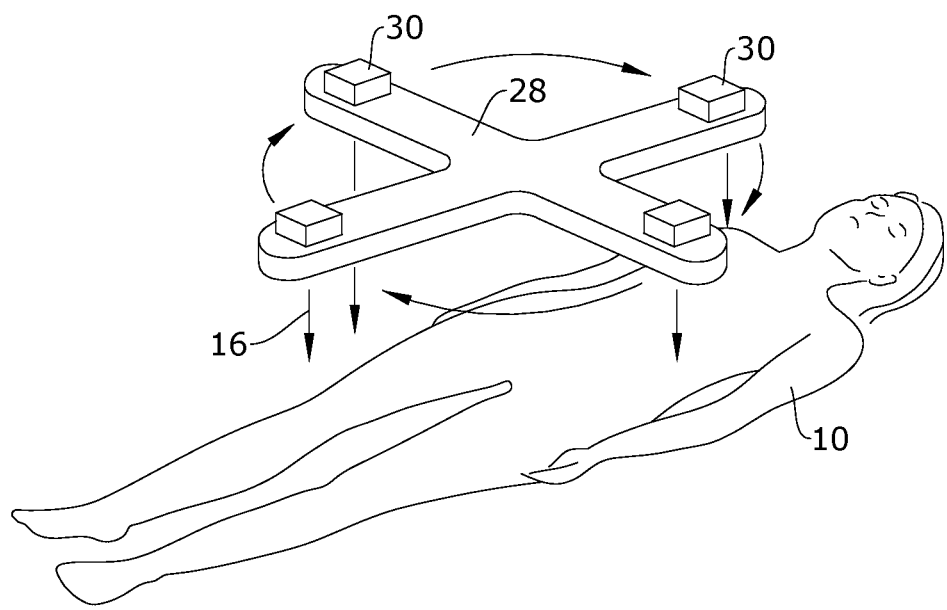
FIG. 6 is a schematic view of a method of viral disruption according to an embodiment of the present invention, showing a subject lying beneath an alternating current (AC) strong magnetic field formed by rotating magnets.

FIG. 6 shows a system of spatially swirling very strong neodymium permanent magnets 30 mounted onto a non-magnetic substrate or non-metallic rotatable base 28 to generate an alternating, spatially varying magnetic field 16 over time (i.e., AC Magnetics) in a repeatable controlled fashion over and/or under stationary targets such as the patient 10.

Figure 7:
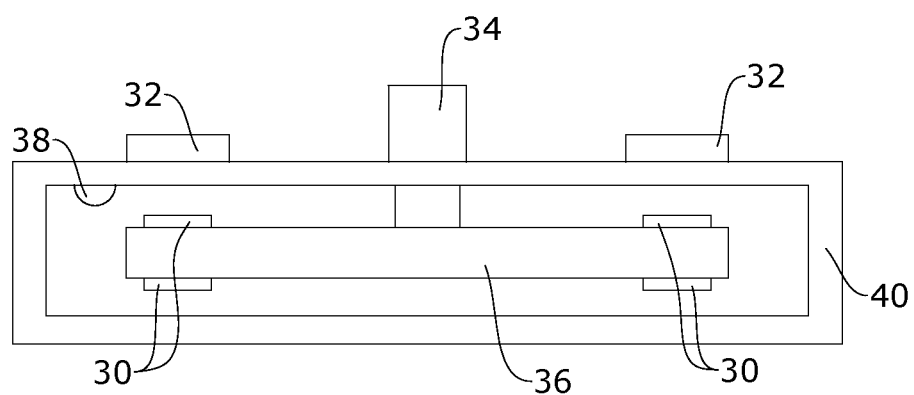
FIG. 7 is a schematic view of a method of viral disruption according to an embodiment of the present invention, showing specimen dishes resting above an alternating strong magnetic field formed by rotating magnets.

The inventive system may also be used to expose samples (comprising host cell, viral particles and, for some samples, MiPcL substances) contained within specimen dishes 32 to a magnetic field, with the specimen dishes 32 resting on an oscilloscope 38 non-magnetic frame 40, as shown in FIG. 7, using magnets 30 mounted on a rotating base 36 operated by a motor 34. Diagnosis of the efficacy of the AC magnetic viral disruption may be accomplished by staining or electron microscopy of the specimens, before and after the AC magnetic fields are applied.

It should be understood, of course, that the foregoing relates to exemplary embodiments of the invention and that modifications may be made without departing from the spirit and scope of the invention as set forth in the following claims.

What is claimed is:

1. A therapeutic method of reducing or eliminating viral infections in vivo comprising:

providing a virus disruption apparatus having a magnetic field generator operative to generate a static magnetic field greater than ambient magnetic fields; and subjecting a virally infected patient to the static magnetic field generated by the virus disruption apparatus with a magnetic field intensity effective to disrupt viral metabolism by reorienting at least one compound selected from the group consisting of: ferritin, ferroportin, and viral components.

2. The therapeutic method of claim 1, wherein the magnetic field intensity is up to 1 to 10 Tesla.

3. The therapeutic method of claim 1, further comprising administering magnetic nanoparticles to the virally infected patient prior to subjecting the virally infected patient to the static magnetic field.

4. The therapeutic method of claim 1, further comprising administering at least one antiviral pharmacological composition to the virally infected patient prior to subjecting the virally infected patient to the static magnetic field.

5. The therapeutic method of claim 1, wherein the magnetic field generator is selected from the group consisting of: a Magnetic Resonance Imaging apparatus, one or more permanent magnets, a superconducting magnet, a cyclotron, a solenoid, and combinations thereof.

6. The therapeutic method of claim 5, wherein the magnetic field generator is neodymium permanent magnets mounted onto a non-magnetic substrate.

7. The therapeutic method of claim 1, wherein the magnetic field intensity is at least 0.5 Tesla.

8. A method of disrupting viral metabolism comprising:

providing a virus disruption apparatus having a magnetic field generator operative to generate an alternating magnetic field greater than ambient alternating magnetic fields; and subjecting an infected patient or a live host cell and viral mixture to the alternating magnetic field generated by the virus disruption apparatus with a magnetic field intensity of at least 0.1 nanoTesla in a frequency range between 3 and 40 Hz, effective to disrupt viral metabolism by reorienting at least one compound selected from the group consisting of: ferritin, ferroportin, and viral components.

9. The method of claim 8, further comprising administering magnetic nanoparticles to the infected patient prior to subjecting the infected patient to the alternating magnetic field.

10. The method of claim 8, further comprising administering at least one antiviral pharmacological composition to the infected patient prior to subjecting the infected patient to the alternating magnetic field.

11. The method of claim 8, wherein the magnetic field generator is selected from the group consisting of: a Magnetic Resonance Imaging apparatus, one or more permanent magnets, a superconducting magnet, a cyclotron, a solenoid, and combinations thereof.

12. The method of claim 11, wherein the alternating magnetic field is an intermittent magnetic field generated by switching the apparatus on and off.

13. The method of claim 11, wherein the alternating magnetic field is generated by rotating the one or more permanent magnets and has a magnetic field intensity of at least 0.01 Tesla.

14. The method of claim 11, wherein the one or more permanent magnets is a plurality of permanent magnets and the alternating magnetic field is generated by the plurality of permanent magnets mounted on a rotatable non-magnetic base.

15. The method of claim 8, wherein the magnetic field intensity is up to 3 Tesla.

16. A method of disrupting viral metabolism comprising:

providing a plurality of permanent magnets mounted on a rotatable non-magnetic base operative to generate an alternating magnetic field with a magnetic field intensity of at least 1 nanoTesla; and providing a live host cell and viral mixture contained within a specimen dish resting on a non-magnetic frame surrounding the rotatable non-magnetic base; and subjecting the live host cell and viral mixture to the alternating magnetic field.

* * * * *